(12) United States Patent
Nacouzi

(10) Patent No.: US 6,354,710 B1
(45) Date of Patent: Mar. 12, 2002

(54) AROMATIC SYSTEM AND METHOD OF USE

(76) Inventor: George J. Nacouzi, 415 Herondo St. Apt. 211, Hermosa Beach, CA (US) 90254

(*) Notice: Subject to any disclaimer, the term of this patent is extended or adjusted under 35 U.S.C. 154(b) by 0 days.

(21) Appl. No.: 09/656,185

(22) Filed: Sep. 6, 2000

(51) Int. Cl.⁷ .............................................. F21V 33/00
(52) U.S. Cl. ........................ 362/96; 362/253; 431/289; 422/5; 422/125; 219/220
(58) Field of Search ................... 362/96, 253; 219/201, 219/209, 220; 422/120, 125, 5; 431/289; 392/390

(56) References Cited

U.S. PATENT DOCUMENTS

| | | | | |
|---|---|---|---|---|
| 2,469,656 A | * | 5/1949 | Lienert | 422/125 |
| 3,748,464 A | * | 7/1973 | Andeweg | 362/355 |
| 5,032,360 A | * | 7/1991 | Houston | 422/4 |
| 5,395,233 A | * | 3/1995 | Karp | 431/289 |
| 5,651,942 A | * | 7/1997 | Christensen | 422/125 |
| 5,744,106 A | * | 4/1998 | Eagle | 422/306 |
| 6,106,786 A | * | 8/2000 | Akahoshi | 422/124 |
| 6,196,706 B1 | * | 3/2001 | Cutts | 362/392 |

* cited by examiner

Primary Examiner—Thomas M. Sember
(74) Attorney, Agent, or Firm—Ted Masters

(57) ABSTRACT

An aromatic system (20) includes an aromatic member (22) such as a candle which includes a fragrance (25) disposed within wax, and a flameless heat source (24). Aromatic member (22) is disposed in the proximity of heat source (24) so that when heat source (24) is energized it melts the wax and releases fragrance (25). Heat source (24) can be a light or lamp, or alternatively can be a warming device (124) such as a hot plate.

8 Claims, 2 Drawing Sheets

AROMATIC SYSTEM AND METHOD OF USE

TECHNICAL FIELD

The present invention pertains generally to aromatic candles which emanate a fragrance, and in particular to an aromatic system wherein the system does not utilize a lighted wick, but rather uses an external flameless source of heat to melt the candle wax and release the fragrance.

BACKGROUND ART

Aromatic candles are well known in the art. When the wick of the candle is burned, the candle wax melts causing the release of an aromatic fragrance contained within the wax. The fragrance can both be pleasing to smell, and also can have therapeutic value. Fragrances can also be dispensed in other ways. For example, U.S. Pat. No. 5,908,231 discloses an improved fragrance dispenser of safe, simple and inexpensive design is reusable and can be utilized on a light bulb regardless of orientation of the bulb. The fragrance dispenser securely grips the light bulb at its widest point such that the light bulb may be oriented in any direction. Thus the fragrance dispenser may be used, for example, on a telescoping desk lamp or a swinging lamp where the bulb can be oriented in any direction not merely base up or base down. The fragrance dispenser is made from absorbent material that is non-combustible and reusable, such that the absorbed fragrance oil is vaporized to scent the room air with a pleasing fragrance when the light bulb is turned on and heat is generated.

DISCLOSURE OF INVENTION

The present invention is directed to an aromatic system, and comprises a new and more efficient way to cause current and/or modified aromatic candles to emanate their fragrance. Currently, a burning wick in the candle melts the wax thereby causing the fragrance to evaporate. The device described herein uses a flameless radiating heat source, i.e., a warm plate or light to melt the wax, causing the fragrance to evaporate. In its most basic form, the aromatic system of the present invention uses a halogen light that focuses light on the (top or other) surface of an aromatic candle (or a warm plate conducting heat onto the surface of the candle). The light (or warm plate) heats the candle surface and causes the wax to melt, thereby releasing the fragrance. It may also be appreciated that the aromatic system of the present invention is self contained, and may be constructed to provide an unlimited variety of aesthetically pleasing designs.

Several features can be added to the aromatic system of the present invention. First, the relative distance between the light source and the candle surface can be adjusted to control the amount and intensity of light projected onto the candle's surface. Second, a dimmer may be used to control the intensity of the light and third, a variable focus can be used to control the amount and intensity of light impinging on the candle surface. These options allow for the effective use of different sized candles. Additionally, the present invention can be designed as a tabletop or be mounted on a wall. The candle used with the device herein can be a standard aromatic candle or a modified candle to produce an aesthetic design. The candle used does not require a wick, but may have one to allow the candle to be used by burning in a standard way. Additionally, the modified candle could have a chemical composition that is optimized for use with the system of the present invention.

Advantages of the Present Invention

1. The conventional approach in using an aromatic candle is to light the wick, which causes local melting of the wax and the subsequent release of aroma. There are several draw backs to this process:

a) Release of combustion products from the wick such as soot and small amounts of toxins such as acetone, benzene, lead and mercury into the air. Some of the wicks being used today in aromatic candles have metallic compounds to slow down their burn rate. These wicks release lead into the air that may end up being inhaled. Conversely, the present invention is clean, environmentally friendly and releases zero combustion products since the heat source is flameless.

b) The fragrance released by a standard burning candle is mixed with combustion products that decrease their aromatic effectiveness. The present invention has no combustion products so that the fragrance being released is much cleaner and more effective, so it can be detected sooner and has a stronger effect.

c) The use of burning candles has some inherent risks associated with starting a fire. Studies have determined that a number of fires in the U.S. are started by burning candles. On the other hand, The present invention does not have any flames associated with it, so the risk of fire is almost eliminated. The risk of fire is that associated with a low wattage light (about 20 W) which is insignificant with a proper design.

d) The typical life of a medium size (a 4 inch high by 2 inch diameter cylindrical shape) aromatic candle is about 24 hours. The same candle used with the present invention can last anywhere between 4 to 10 times longer, depending on design specifications related to radiance at the surface of the candle. The 4 to 10 times value is based on representative test results performed by the inventor. Additionally, unlike standard candles, the present invention (with or without the aromatic candle inserted) can be left on for long periods of time.

e) A burning candle starts losing its form in a matter of minutes (depending on the design of the candle), however, with the present invention, the candle will retain its form for many hours (depending on the shape and the relative location of the light source). Also with a judicious candle design, the candle can be made to retain its external shape for a much longer period.

2. The present invention is also a light source (a lamp) that can be used without a candle. Note that the specific design of the present invention is very flexible and can be made to fit different aesthetic requirements, wherein decorative housings or containers surround the candle.

In accordance with a preferred embodiment of the invention, an aromatic systems includes a flameless heat source and an aromatic member including a fragrance disposed within wax. The aromatic member is disposed in the proximity of heat source, so that when the heat source is energized the heat source melts the wax and releases the aromatic fragrance.

In accordance with an important aspect of the invention, the aromatic member can either have or not have a wick.

In accordance with an important feature of the invention, the flameless heat source may be either a light or a warming device such as a hot plate.

In accordance with another important aspect of the invention, the heat source has an adjustable intensity control.

In accordance with another preferred embodiment of the invention, a structure for releasing fragrance from an aromatic member, includes a light, and a platform for accepting the aromatic member, so that when the aromatic member is placed upon the platform and the light is energized, heat from the light melts the aromatic member.

Other features and advantages of the present invention will become apparent from the following detailed description, taken in conjunction with the accompanying drawings, which illustrate, by way of example, the principles of the invention.

MODES FOR CARRYING OUT THE INVENTION

Figure 1:
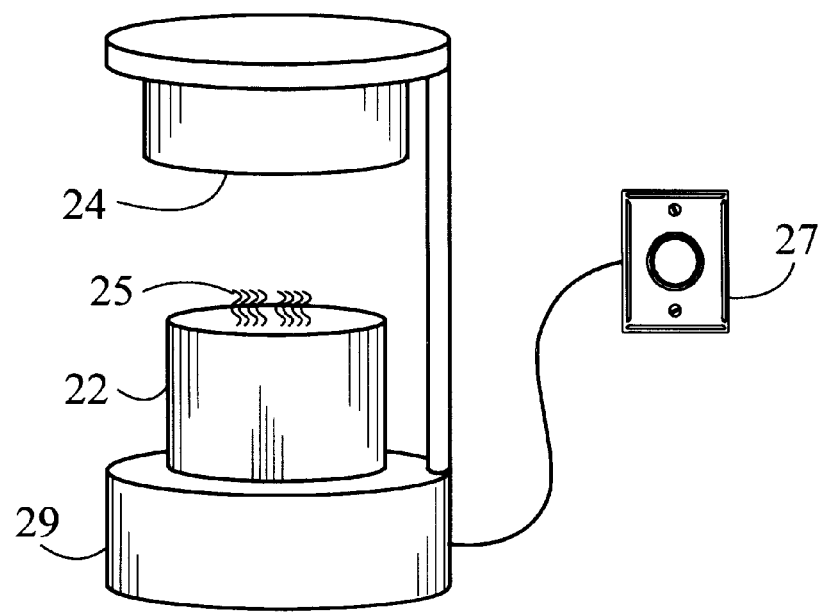
FIG. 1 is a perspective view of an aromatic system in accordance with the present invention.

Referring initially to FIG. 1, there is illustrated a perspective view of an aromatic system in accordance with the present invention, generally designated as 20. Aromatic system 20 includes an aromatic member 22 including a fragrance disposed within a wax body. In preferred embodiments, aromatic member 22 is a candle-like structure that can either contain a wick 26 (refer to FIG. 3), or not contain a wick as is shown in FIG. 1. Aromatic member 22 can be of any convenient shape such as that of a cylinder as shown, and resides upon a platform 29. Aromatic member 22 is disposed in the proximity of a flameless heat source 24, so that when heat source 24 is activated it melts the wax and releases the fragrance 25. In a preferred embodiment, heat source 24 is a light, either a halogen light or an incandescent light. A halogen light which provides approximately 20 watts of power has been found useful. Also in a preferred embodiment the light has an adjustable intensity control 27 so that the amount of heat delivered to aromatic member 22 may be controlled. A heat enhancer, such as a parabolic reflector, can be utilized to focus the light and heat thereby reducing the amount of energy required to melt the wax.

Figure 2:
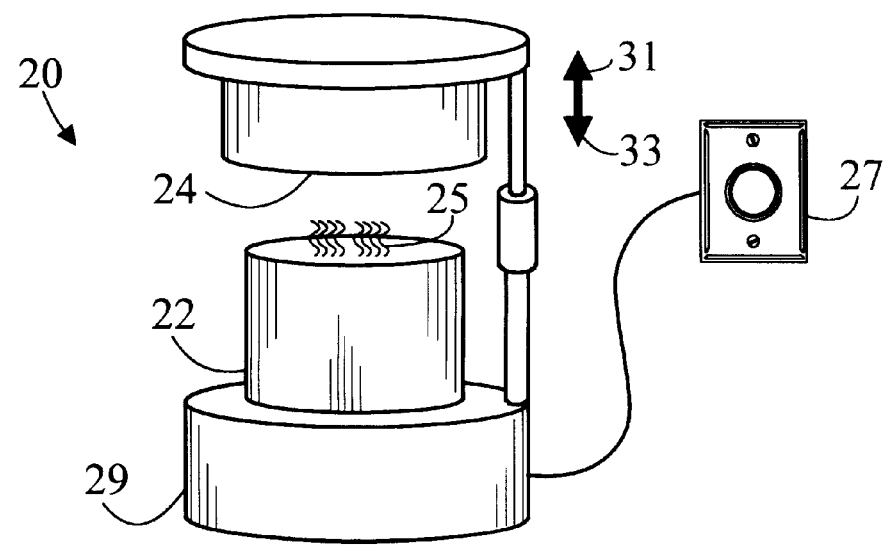
FIG. 2 is a perspective view of a alternate aromatic system wherein the distance between an aromatic member and a heat source may be selectively adjusted.

FIG. 2 is a perspective view of a alternate aromatic system 20 wherein the distance between an aromatic member 22 and a heat source 24 may be selectively adjusted. Heat source 24 is selectively positionable in directions 31 and 33 with respect to aromatic member 22.

Figure 3:
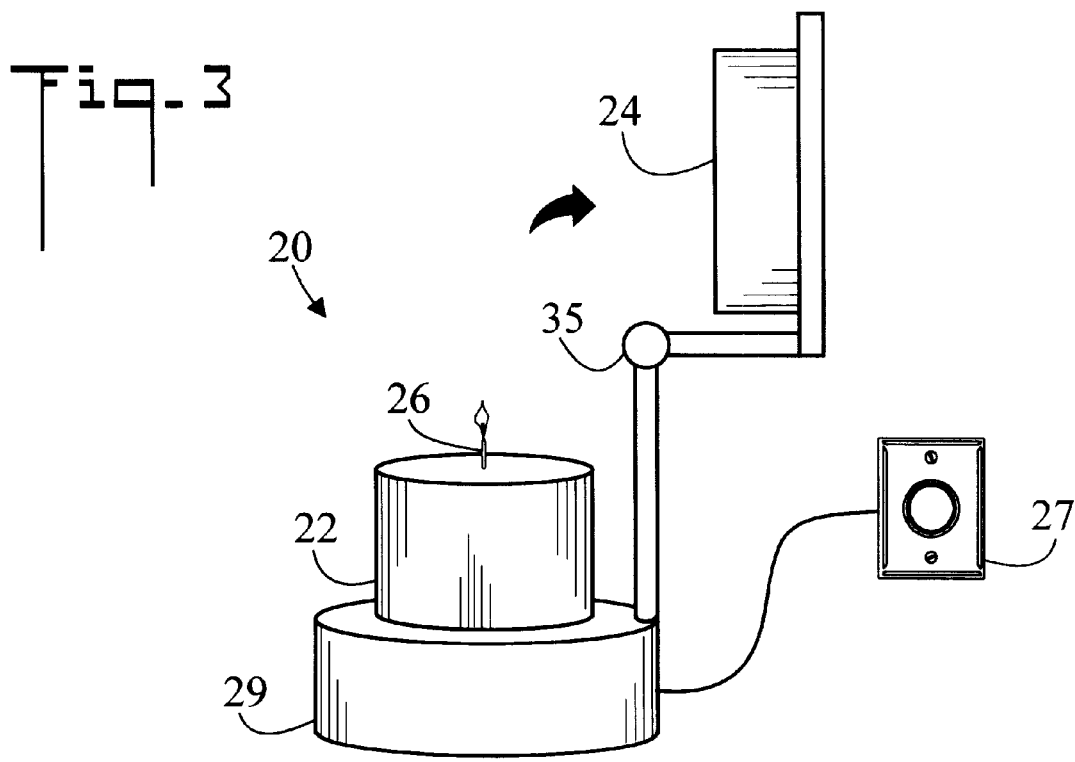
FIG. 3 is a perspective view of another alternate aromatic system wherein the heat source may be selectively positioned away from an aromatic member having a lighted wick; and, FIG. 4 is a perspective view of a second embodiment aromatic system which uses a warming device such as a hot plate.

FIG. 3 is a perspective view of another alternate aromatic system 20 wherein the heat source 24, such as a light, may be selectively positioned away from aromatic member 22 having a lighted wick, so the flame will not damage heat source 24. In the shown embodiment, a pivot 35 allows heat source 24 to be rotated away from aromatic member 22.

Figure 4:
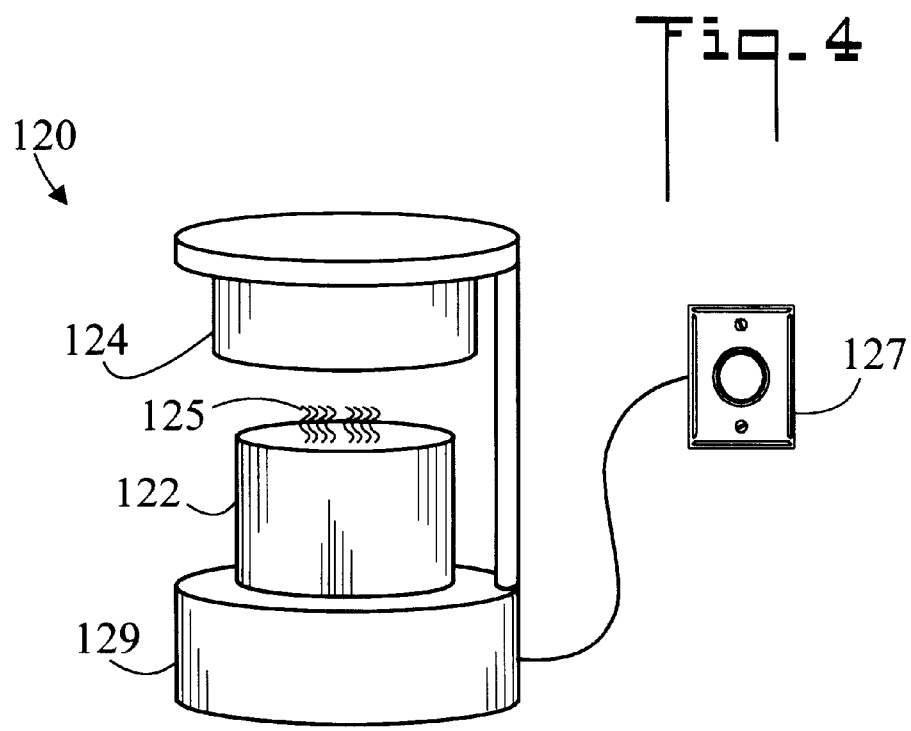

FIG. 4 is a perspective view of a second embodiment aromatic system which uses a warming device, generally designated as 120. In this embodiment, heat source 124 includes a warming device such as a hot plate. The warming device can have an adjustable heat control 127.

In terms of use, a method for releasing a fragrance 25 comprises:

providing an aromatic system 20 including an aromatic member 22 including a fragrance 25 disposed within wax;

providing a flameless heat source 24, such as a light or lamp; and, placing the aromatic member 22 in the proximity of the heat source 24, so that when the heat source 24 is energized it melts the wax and releases the fragrance 25.

Since many users of the present invention will be using regular scented candles, there is a concern that some consumers may also light the wick of the candle while it is in the device. The design of the device will address this concern by considering different approaches that will minimize the impact of the subject adverse action.

1. Clear directions will warn the consumer against lighting the candle's wick while in the device. It will be recommended that the wick be trimmed, after each use, to be flush against the surface of the candle.
2. The location of the light source will be either offset at an angle, recessed back from the wicked surface of the candle to prevent damage from occurring to the light source if the wick is lit while in the device, or positionable as is shown in FIG. 3.
3. A wickless candle will be made available to use with the device, this approach will eliminate the problem as long as the consumer does not insert a regular candle in the device.

The basic design of the subject device involves a platform where the candle is placed and a focused light source, 20 W for best results (halogen or other), strategically placed to focus on a given surface of the candle.

The preferred embodiments of the invention described herein are exemplary and numerous modifications, dimensional variations, and rearrangements can be readily envisioned to achieve an equivalent result, all of which are intended to be embraced within the scope of the appended claims.

I claim:

1. An aromatic system, comprising:

a focused light source having a support;

an aromatic candle having a wick;

said aromatic candle including a fragrance disposed within wax;

a candle support connected to said light source support so as to position the candle in the proximity of said light source; and, so that when said light source is energized light and heat from said light source melts said wax and releases said fragrance.

2. An aromatic system according to claim 1, further including:

said light source and said aromatic candle selectively positionable with respect to each other.

3. An aromatic system according to claim 1, further including:

a reflector for focusing light and heat from said light source upon a surface of said aromatic candle.

4. An aromatic system according to claim 1, further including:

said light source having an adjustable intensity.

5. An aromatic system according to claim 1, further including:

said light source being a halogen light.

6. An aromatic system according to claim 5, further including:

said halogen light dissipating about 20 watts of power.

7. An aromatic system according to claim 1, further including:

a reflector for focusing light and heat from said light source upon a surface of said aromatic candle; and, said light source being a halogen light which dissipates about 20 watts of power.

8. A method for releasing a fragrance, comprising:
(1) providing an aromatic system including:
   a focused light source having a support;
   an aromatic candle having a wick;
   said aromatic candle including a fragrance disposed within wax;

(2) without lighting said wick, placing said aromatic candle on a candle support which is connected to said light source support so as to position the candle in the proximity of said light source; and, (3) so that when said light source is energized light and heat from said light source melts said wax and releases said fragrance.

* * * * *